United States Patent [19]

Izumi et al.

[11] Patent Number: 4,583,018
[45] Date of Patent: Apr. 15, 1986

[54] ELECTRODE CONFIGURATION FOR PIEZOELECTRIC PROBE

[75] Inventors: Mamoru Izumi, Tokyo; Syuuzi Suzuki, Yokohama; Hiroki Honda, Yokohama; Isao Uchiumi, Yokohama, all of Japan

[73] Assignee: Tokyo Shibaura Denki Kabushiki Kaisha, Kawasaki, Japan

[21] Appl. No.: 555,049

[22] Filed: Nov. 25, 1983

[30] Foreign Application Priority Data

Nov. 29, 1982 [JP] Japan ................... 57-207701

[51] Int. Cl.⁴ ............................. H01L 41/08
[52] U.S. Cl. .................... 310/334; 310/365; 310/366
[58] Field of Search ............... 310/334–337, 310/365, 366; 73/632, 633, 649

[56] References Cited

U.S. PATENT DOCUMENTS

| 3,952,387 | 4/1976 | Iinuma et al. ............. 310/334 X |
| 4,211,948 | 7/1980 | Smith et al. .............. 310/334 X |
| 4,217,684 | 8/1980 | Brisken et al. ............ 310/334 X |
| 4,277,712 | 7/1981 | Hanafy ...................... 310/334 |
| 4,395,652 | 7/1983 | Nakanishi et al. .......... 310/334 |
| 4,473,769 | 9/1984 | Nguyen ..................... 310/334 |
| 4,482,834 | 11/1984 | Dias et al. ............. 310/334 X |

FOREIGN PATENT DOCUMENTS 0042407  3/1980  Japan ..................... 310/334

Primary Examiner—Mark O. Budd
Attorney, Agent, or Firm—Schwartz, Jeffery, Schwaab, Mack, Blumenthal & Evans

[57] ABSTRACT

Disclosed is an ultrasonic probe comprising a piezoelectric element in which a first and second electrodes provided respectively on both surfaces of a piezoelectric material are arranged in such a way that said electrodes have end portions facing each other near the center of, and with the interposition of, the piezoelectric material.

13 Claims, 11 Drawing Figures

ELECTRODE CONFIGURATION FOR PIEZOELECTRIC PROBE

BACKGROUND OF THE INVENTION

This invention relates to an ultrasonic probe suitable for use in an ultrasonic diagnostic system, ultrasonic flaw detection system or the like.

An ultrasonic probe produces ultrasonic waves by a piezoelectric element and inspects the internal state of an object on the basis of reflected waves of the ultrasonic waves. Ultrasonic probes are used in a variety of application fields, for example, for diagnoses of the interiors of human bodies and detections of flaws in metal welds.

An ultrasonic beam emitted from a piezoelectric element has conventionally been focused using such means as an acoustic lens so that the resolution can be enhanced, which is called a focused beam method. The focused beam method can certainly provide a high resolution near the focal point. It is however accompanied by a drawback that the resolution is lowered as the point of an inspection or diagnosis moves away from the focal zone.

With a view toward solving the above drawback, ultrasonic probes driven by a synthetic aperture method have been studied. The synthetic aperture method is a method in which fan beams having a large beam width are emitted from a number of measurement points, and a number of pieces of information on the object collected from the measurement points, are synthesized to form a picture image of the object. According to the synthetic aperture method, the resolution is not governed by the distance but is determined by the beam width of each ultrasonic beam. The resolution is improved as the beam width becomes greater. Since a beam width is substantially in inverse proportion to the width of the aperture of the oscillating surface of a piezoelectric element, it is desirous to make the width of each aperture as small as possible. The resultant resolution becomes substantially the same level as the width of the aperture the oscillating surface of the piezoelectric element.

In the case of conventional ultrasonic probes, there was however a limitation to the sizes of piezoelectric elements suitable for use therein. If the width of a piezoelectric element is 5 mm or thinner, the piezoelectric element makes the fabrication of an ultrasonic probe very difficult.

In the case of an array-type ultrasonic probe which uses a plurality of piezoelectric elements, the piezoelectric elements can be obtained by slicing a single piece of piezoelectric element, and their intervals may thus be reduced to several hundred micrometers or so. Supposing that each piezoelectric material has a rectangular shape, one of its sides may hence be shortened to several hundred micrometers or so. However, a width of about 1-2 mm is necessary for connecting leads to the electrodes of a piezoelectric material. Therefore, it is impossible to shorten the length of the other side beyond the above limitation, leading to a limitation to the size of a piezoelectric element itself in its fabrication. Thus, it has been very difficult to reduce the width of the aperture of a piezoelectric element and to enlarge the beam width of an ultrasonic beam.

With the foregoing in view, the present invention has been completed. An object of this invention is to provide an ultrasonic probe which can produce ultrasonic beams having a great beam width.

SUMMARY OF THE INVENTION

This invention provides an ultrasonic probe making use of a piezoelectric element in which first and second electrodes provided respectively on both surfaces of a piezoelectric material are arranged in such a way that said electrodes have end portions facing (or overlapping) each other near the center of, and with the interposition of, the piezoelectric material.

The above-mentioned first and second electrodes are herein meant to be either one of an earth electrode or a signal electrode, respectively. The term "facing of electrodes" as used herein means that the electrodes are facing or overlapping each other in the direction of polarization of the piezoelectric material. In a piezoelectric element of the above-described structure, the piezoelectric material is oscillated practically only at the portion where the electrodes are facing each other. Thus, the width of the aperture of the oscillating surface of the piezoelectric element becomes substantially equal to the width of the portion where the electrodes are facing each other. Accordingly, it is possible to obtain a piezoelectric element having a small aperture width by using a piezoelectric material having substantially the same size as those used conventionally. By using the piezoelectric element having the small aperture width, an ultrasonic beams having a great beam width can be emitted.

When an ultrasonic probe of this invention is driven in accordance with the above-described synthetic aperture method, the resulting ultrasonic probe has a large beam width and the resolution is of the same level as the width of the aperture. Thus, a high resolution can be achieved.

In another embodiment of this invention, an ultrasonic probe is fabricated by using a piezoelectric element in which first and second electrodes provided respectively on both surfaces of a piezoelectric material are arranged in such a way that said electrodes have end portions facing each other near the center of, and with the interposition of, the piezoelectric material and providing a grounded conductive layer on a surface of the piezoelectric element from which surface ultrasonic waves are emitted, with an insulative layer interposed therebetween. In this embodiment, it is possible to bring about such effects that an ultrasonic probe having such a large beam width as mentioned above can be obtained and, in addition, the S/N ratio is improved.

More specifically, since the surface of a piezoelectric material is shielded by providing a grounded conductive layer on a surface of the piezoelectric element from which surface ultrasonic waves are emitted, the piezoelectric element is less affected by external noises and its S/N ratio is thus improved. Such noises tend to occur from a non-electrode portion which is not covered by an electrode, out of the surface of the piezoelectric material from which surface ultrasonic waves are emitted. Thus, the conductive layer may be provided on the non-electrode portion only. It is however preferred to provide the conductive layer over the entire area of the surface of the piezoelectric element from which surface ultrasonic wave are emitted, because the emission characteristics of ultrasonic wave may be adversely affected if the conductive layer is applied on the non-electrode portion only.

In addition, it is possible to avoid spurious oscillations of the first and second electrodes in the above probe, when the electrode which is facing the conductive layer with the piezoelectric material interposed therebetween is caused to have the same potential as the conductive layer. This effect has been derived for the following reasons. If the potential of the electrode which is facing the conductive layer with the piezoelectric material interposed therebetween is different from that of the conductive layer, a voltage is applied to the piezoelectric material because of a difference in potential between the conductive layer and the electrode. There is thus a danger that the piezoelectric material may be oscillated at portions other than the portion where the first and second electrodes are facing each other. These oscillations are spurious and disturb ultrasonic beams to be emitted from the ultrasonic probe.

As has been described, use of an ultrasonic probe according to this invention permits a large beam width and the provision of a grounded conductive layer can provide an ultrasonic probe having a good S/N ratio.

This invention will hereinafter be described in greater detail with reference to the accompanying drawings.

BRIEF DESCRIPTION OF THE DRAWING

FIG. 5 illustrates ultrasonic probes according to further embodiments of the invention, in which

DESCRIPTION OF THE PREFERRED EMBODIMENTS

Figure 1:
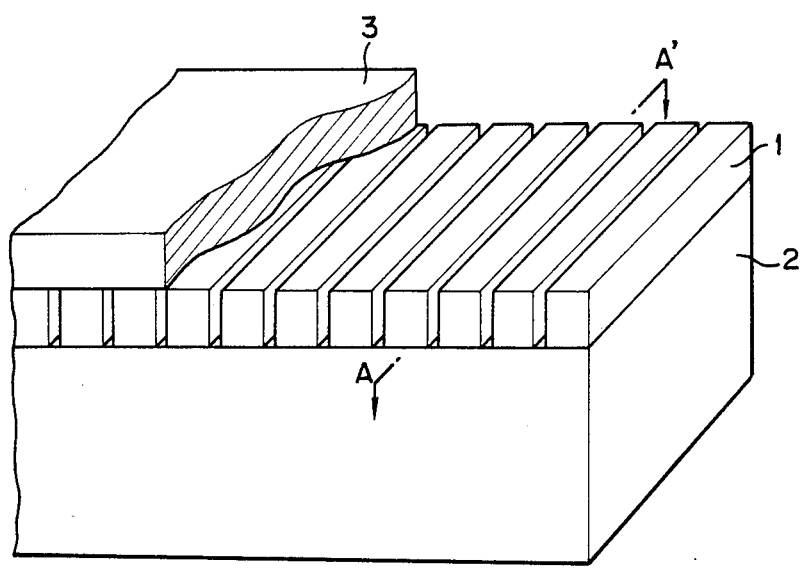
FIG. 1 is a partly cut-away perspective view showing an ultrasonic probe according to one embodiment of this invention.
Figure 2:
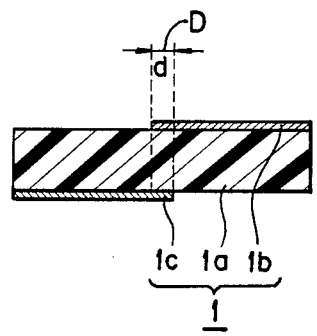
FIG. 2 is a cross-sectional view of the ultrasonic probe, taken line A—A' of FIG. 1.

FIG. 1 is a partially cut-away perspective view of an ultrasonic probe according to one embodiment of this invention. The ultrasonic probe is an array-type ultrasonic probe. A plurality of piezoelectric elements 1 each having a rectangular shape is fixedly mounted on a backing member 2, and the surfaces of the piezoelectric elements 1 from which surfaces ultrasonic waves are emitted are covered by an acoustic matching layer 3. One of the piezoelectric elements 1 is shown in FIG. 2. Namely, FIG. 2 is a cross-sectional view of the piezoelectric element 1, taken along the line A—A' of FIG. 1. A first electrode 1b and a second electrode 1c are provided respectively on both surfaces of the piezoelectric material 1a in such a way that they are partially overlapped near the center of the piezoelectric material 1a to form a portion D where end portions of the electrodes are facing each other. In fabrication of the array-type ultrasonic probe, the portions D of the elements 1 are each arranged in a straight fashion throughout the arrayed piezoelectric elements.

The formation of such a facing portion D may be achieved, for example, by forming electrodes over the entire surfaces of the piezoelectric material, poling the piezoelectric material 1a in its entirety and then forming the first electrode 1b and the second electrode 1c of desired shapes in accordance with a suitable technique such as the etching technique; or by forming the first electrode 1b and the second electrode 1c of desired shapes prior to the poling of the piezoelectric material and then subjecting the piezoelectric material to a poling treatment. In the latter process, the piezoelectric material 1a is partially poled and an internal strain is hence developed in the piezoelectric material 1a. Therefore, the former process is preferred for actual application.

In the case of an ultrasonic diagnostic system for example, a resolution of about 1 mm to 2 mm, namely, a beam width $\theta \div 13°$ or so is required for such purposes as discovering an affected part in a body at an early stage. Supposing that the frequency is 3.5 MHz and water is used as a transmission medium, it is necessary to reduce the aperture width to 2 mm or so. However, it is very difficult to form a piezoelectric element itself into 2 mm or so in view of its fabrication, especially in the case of an array-type ultrasonic probe. However, it becomes readily feasible to design the width d of the facing portion D below about 2 mm or so by employing such a structure as depicted in FIG. 2, thereby providing with ease a piezoelectric element which meets the aforementioned requirements. Since the oscillating surface has a width somewhat broader than the facing portion D where the end portions of the electrodes are facing each other, it is preferable to form the width d into about one-half of the required width, for example, 1 mm or narrower.

Figure 3:
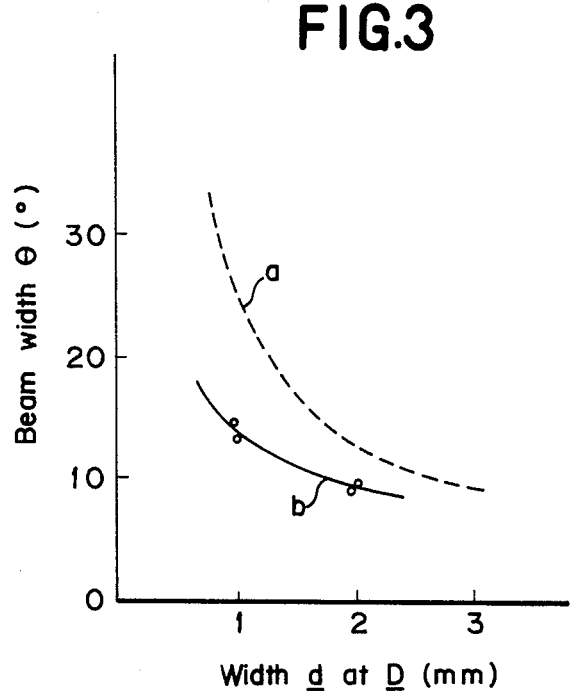
FIG. 3 is $\theta$-d curvilinear diagram showing the relationship between the beam width $\theta$ and the width d of the portion of a piezoelectric material where the electrodes are facing each other.

FIG. 3 illustrates the relationship between aperture width and beam width. The curve a corresponds to theoretical data of the beam width $\theta$ when the width d of the facing portion D is hypothetically considered to be equal to the aperture width. On the other hand, the curve b indicates experimental data of the beam width $\theta$ for various widths d of the facing portion D. As readily envisaged from FIG. 3, the experimental data have smaller beam widths $\theta$ than the theoretical data. As described above, it is thus preferred to make the width d of the required facing portion D smaller than its theoretical value.

Since the aperture width of a piezoelectric element can be readily made narrower by incorporating such a structure as described above, it is possible to obtain an ultrasonic probe which can emit ultrasonic beams having a large beam width. Moreover, since the facing portion D has been formed near the centre of the piezoelectric element, ultrasonic beams having uniform width can be emitted.

Figure 4:
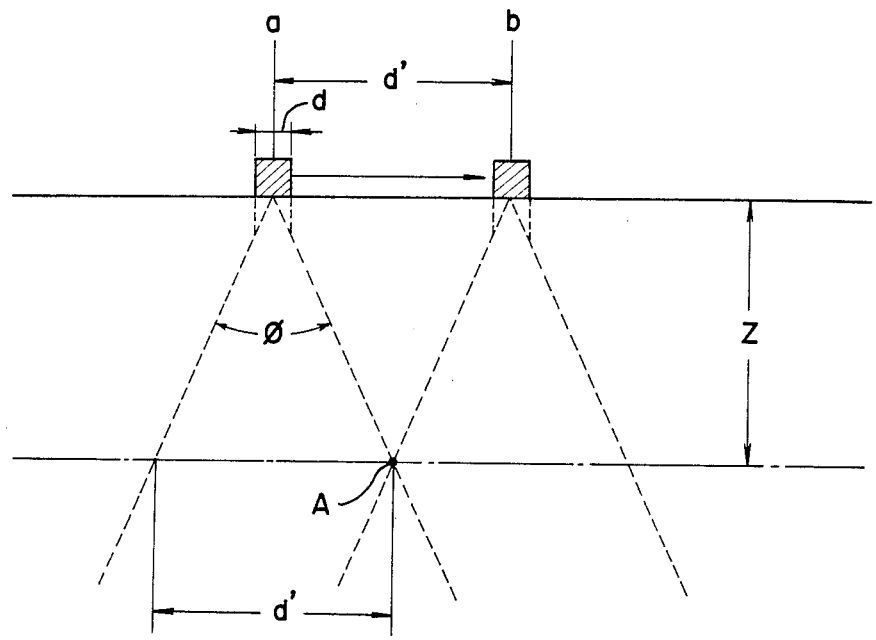
FIG. 4 is schematic illustration of the detection of a flaw by an ultrasonic probe.

In the synthetic aperture method, detection of a flaw or the like is carried out by scanning an object with a piezoelectric element which, as mentioned above, has a small aperture width d and can emit ultrasonic beams having a large beam width. FIG. 4 schematically illustrates the detection of a point A located in an object o with a distance Z apart from the surface of the object o. Using an ultrasonic beam width $\phi$, the information of the point A is obtained at various points along the scanning distance d' in the drawing. In the synthetic aperture method, the thus-collected pieces of information are synthetically processed to achieve a resolution of a level similar to the length of the width d.

The beam width $\phi$ of a piezoelectric element having an aperture width d is approximated with $\lambda/d$ in which $\lambda$ means the wavelength of an ultrasonic wave.

The beam width $\theta$ by the synthesized aperture width d' is approximated with $\lambda/d'$.

Owing to the relationship of $$\frac{d'}{2} = Z \cdot \tan\frac{\phi}{2}, \quad d' = 2Z \cdot \tan\frac{\phi}{2}$$

may be approximated with $Z\phi$ when $\phi/2$ is small. The resolution $\Delta X = Z \cdot \tan\theta$ may on the other hand be approximated with $Z\theta$, because $\theta$ is generally small. Hence, $$\Delta X \sim Z\theta \sim \lambda/d' \cdot z \sim \frac{\lambda z}{\phi z} \sim \frac{\lambda}{\lambda/d} \sim d.$$

Therefore, it is possible to obtain a resolution of substantially the same level as the aperture width.

When the width d of the facing portion was set at 1 mm in an ultrasonic probe having such a structure as mentioned above and the resultant ultrasonic probe was driven in accordance with the synthetic aperture method, it was possible to obtain resolutions of about 1 to 1.5 mm irrespective of the depth of an interested part in an object. In the present invention, it is thus possible to achieve a high resolution level irrespective of the depth of each interested part in an object, namely, over a wide range of depths. The reliability of flaw detection can thus be improved if the present invention is used, for example, in an ultrasonic flaw detection system. When the present invention is applied to an ultrasonic diagnostic system, high resolutions are available over a wide range of depths. Therefore, it becomes possible for example to achieve early-stage discovery of breast cancers and the like.

Furthermore, the above ultrasonic probe may be applied to process signals by the synthetic aperture method in the A—A' direction of FIG. 1 and the direction of alignment of a plurality of piezoelectric elements may be set by the focused beam method.

The greater the ultrasonic beam width $\theta$ is made, the more information from the respective piezoelectric elements can be obtained, thereby obtaining a higher resolution. In practical use, the width $\theta$ kept at the level of about 10° or a little wider is very effective.

Figure 5A:
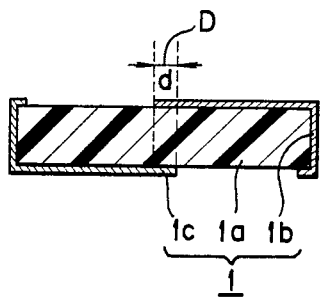
FIGS. 5(a) and 5(c) are cross-sectional view of the ultrasonic probes and FIG. 5(b) is a top plan view of the ultrasonic probe.
Figures 5B, 5C:
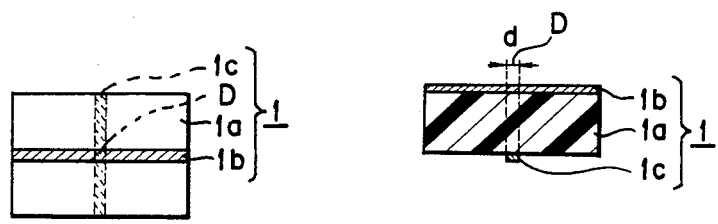

Other embodiments of this invention will next be described. FIGS. 5(a) and 5(c) are cross-sectional views of piezoelectric elements whereas FIG. 5(b) is a plan view of a piezoelectric element 1. In these drawings, the manner of formation of the facing portion D by the first and second electrodes 1b, 1c of the piezoelectric material 1a is changed. Other parts are the same as those depicted in FIG. 1.

In FIG. 5a, outward ends of the electrodes 1b, 1c are both extended to their corresponding side walls of the piezoelectric material so as to facilitate the leading-out of the electrodes. In FIG. 5(b), the facing portion D is formed by allowing the elctrodes 1b, 1c to cross each other. By taking such a structure, the control in width of the facing portion D is rendered easier. In such a structure as shown in FIG. 2, the facing portion D is determined by the extent of overlapping of the electrodes 1b, 1c. It is however determined by the widths of the electrodes 1b, 1c irrelevant to the way of their overlapping in the case of FIG. 5(b). FIG. 5(c) illustrates another embodiment of piezoelectric element in which the first electrodes 1b is applied on the entire area of one of the surfaces of the piezoelectric material 1a but the second electrode 1c is provided on a part of the other surface. Owing to the adoption of such a structure as shown in FIG. 5(c), the width of the facing portion D is determined by the width of the second electrode 1c only, thereby facilitating the control of the width of the facing portion D.

In the above embodiments, the piezoelectric elements were fabricated into array-type ultrasonic transducers. It is however possible to bring about substantially the same effects as an array-type ultrasonic transducer by causing a single-type ultrasonic probe, which is formed of a single piece of piezoelectric element, to scan mechanically.

A still further embodiment of this invention in which a conductive layer is provided will next be described.

Figure 6:
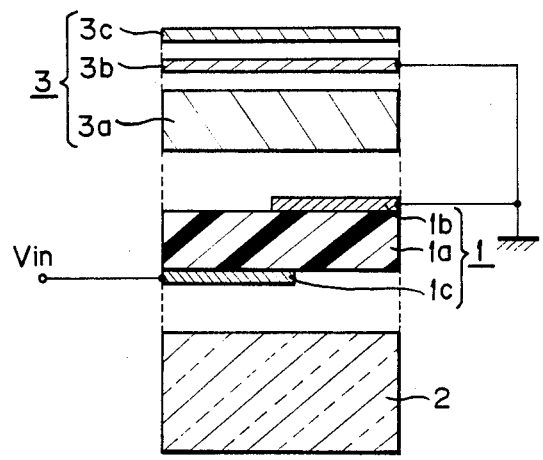
FIGS. 6 to 9 are cross-sectional views respectively illustrating ultrasonic probes according to still further embodiments of this invention.

FIG. 6 is a cross-sectional view of a piezoelectric element and acoustic matching layer.

The piezoelectric element 1 in the present embodiment has the same structure as the piezoelectric element depicted in FIG. 2. The acoustic matching layer 3 has been formed by successively laminating an insulating layer 3a, a conductive layer 3b and a protective layer 3c in order. These layers are arranged in such a way that the protective layer 3c constitutes the outermost layer.

The conductive layer 3b can be provided, for example, by coating a conductive paste, depositing a metal or adhering a metal foil. It is preferred to make the thickness of the conductive layer 3b sufficiently thin relative to the wavelength so that the conductive layer 3b does not impair the emission and reception of ultrasonic waves by the piezoelectric element. The suitable thickness is of the level of 10 $\mu$m or so.

The protective layer 3c is provided to protect the conductive layer 3b. A polymer film having excellent resistance to water and oil and electrically-superb insulating property such as insulating varnish, polyimide, polyester or the like is used. It is also preferred to make the protective layer 3c sufficiently thin, preferably about 10 $\mu$m in thichness, relative to the wavelength so that the protective layer 3c does not impair the emission and reception of ultrasonic waves by the piezoelectric element. Where it is unnecessary to provide the conductive layer 3b with resistance to water, oil, etc., it is not required to provide the protective layer 3c additionally. It is however preferred to provide, generally speaking, the protective layer 3c because an ultrasonic probe is normally used to emit ultrasonic waves into an object through water, oil or the like.

Such conductive layer 3b and protective layer 3c may be provided at once if a printed flexible sheet having a conductive layer such as copper foil and made of a polyester, polyimide or the like is used. This is very advantageous from the viewpoint of fabrication. Where the insulating layer 3a is formed of a plurality of layers, it is unnecessary to provide any additional protective film if the conductive layer 3b is provided between such insulating layers.

The acoustic matching layer 3 is formed generally with a thickness equivalent to one-fourth of the wavelength $\lambda$ of ultrasonic waves. The acoustic matching layer has heretofore been formed of an insulating layer only. Thus, the insulating layer has conventionally had a thickness of $\lambda/4$. In the present embodiment, it is preferred to adjust the thickness of the insulating layer 3a so that the total thickness of the insulating layer 3a, conductive layer 3b and protective layer 3c becomes λ/4 because the conductive layer 3b and protective layer 3c are provided additionally.

Using a printed flexible sheet (70 μm thick including the layer of an adhesive) made of 18 μm-thick Cu and 25 μm-thick polyimide as a conductive and protective film and making the portion of a piezoelectric element at which portion the electrodes are facing each other be 1 mm, an ultrasonic probe of the aforementioned structure was fabricated. The ultrasonic probe was then driven in accordance with the synthetic aperture method. By using the above-fabricated ultrasonic probe having the above-described structure, a resolution of the level of 1 to 1.5 mm or so was achieved irrespective of the depth of an interested point in an object. The ultrasonic probe was free from the intrusion of noises from the outside and gave a dynamic range of 80 dB or higher and a good S/N ratio.

Figure 7:
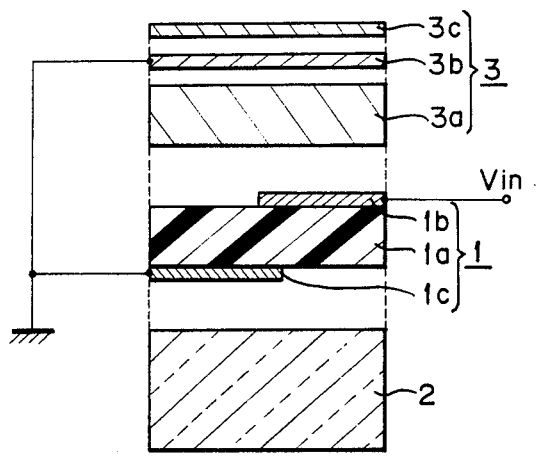
Figure 8:
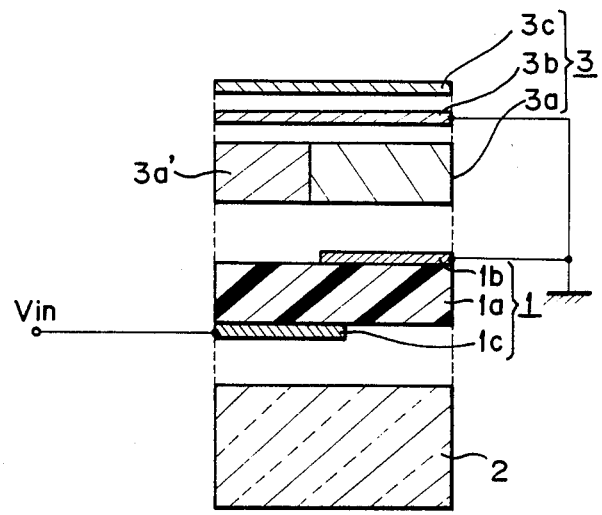

Still further embodiments of this invention in which conductive layers are provided are illustrated respectively in FIGS. 7 and 8.

The embodiment shown in FIG. 7 has the same structure as the embodiment depicted in FIG. 6 except that the combination of grounding of the electrodes 1b, 1c and the conductive layer 3b has been changed. FIG. 7 is a cross-sectional view similar to FIG. 6.

In this embodiment, the conductive layer 3b and the electrode 1c which is located at the side of the backing member 2 are grounded whereas a voltage is applied to the electrode 1b.

Conventioally, the electrode 1b located on the ultrasonic wave emitting surface, of the electrodes of the piezoelectric element 1, was grounded and a voltage was applied to the elctrode 1c positioned at the side of the backing member 2, not only as a countermeasure for the above-described noises but also for avoiding electrical effects due to leakage of currents from the ultrasonic probe to the outside such as electric shock and the like. The conductive layer 3b which is provided to form an electromagnetic shield was also grounded as shown in FIG. 6. In this case, the potential between the conductive layer 3b and electrode 1c may be applied to a non-electrode portion of the ultrasonic wave emitting surface of the piezoelectric element 1 which portion is not covered by the electrode 1c and spurious oscillations may thus be developed.

Provision of the conductive layer 3b as in the present invention can prevent electrical effects to the outside, whereby making it unnecessary to additionally ground the electrode 1c placed on the ultrasonic wave emitting surface of the piezoelectric element 1. As illustrated in FIG. 7, the electrode 1c is thus grounded when driving the ultrasonic probe. Where such a structure as mentioned above is employed, no potential difference is allowed to occur between the electrode 1c and conductive layer 3b and there is thus no danger to produce such spurious osillations as mentioned above.

It is also possible to avoid such spurious oscillations as mentioned above without changing the way of grounding in such a manner as employed in the embodiment illustrated in FIG. 7. The embodiment of this invention, which is shown in FIG. 8, is fabricated by using a material, in which ultrasonic waves are attenuated considerably, to form an insulating member 3a' for a part which is in contact with a non-electrode portion of the ultrasonic wave emitting surface of the piezoelectric element 1 which portion is not covered by the electrode 1b. The remaining parts of the structure is similar to those of the embodiment shown in FIG. 6. FIG. 8 is a cross-sectional view similar to FIG. 6.

In an ultrasonic probe having such a structure as illustrated in FIG. 8, spurious oscillations are prevented from emitting their corresponding ultrasonic waves to the outside even if such spurious oscillations are produced, owing to the provision of the insulating member 3a' made of a material in which ultrasonic waves are attenuated considerably. Accordingly, the ultrasonic probe of FIG. 8 can bring about practically the same effect as an ultrasonic probe in which occurrence of spurious oscillations has been prevented.

Figure 9:
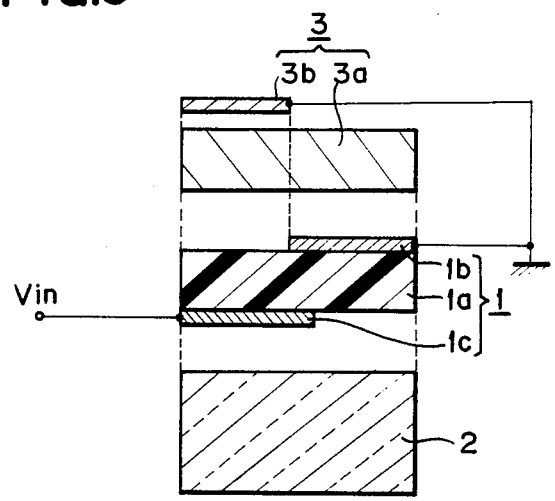

It is not always necessary to have the conductive layer 3b cover the entire area of the surface of the piezoelectric element 1. In a still further embodiment of this invention illustrated in FIG. 9, the conductive layer 3b is provided on a part of the corresponding surface of the piezoelectric element 1 with the insulating layer 3a interposed therebetween. The remaining parts of the structure are the same as those of the embodiment illustrated in FIG. 6. FIG. 9 is a cross-sectional view similar to FIG. 6. In this embodiment, the conductive layer 3b is applied in such a way that it covers only a part of the ultrasonic wave emitting surface of the piezoelectric element 1 which part is not covered by the electrode 1b. The electrode 1b serves as a shield for the surface of the piezoelectric element 1. Thus, intrusion of electromagnetic noises from the outside can be successfully avoided when only the part of the surface, which part is not covered by the electrode 1b, is covered by the conductive layer 3b.

We claim:

1. An ultrasonic probe comprising (a) a piezoelectric element in which first and second electrodes provided respectively on both surfaces of a piezoelectric material are arranged in such a way that said electrodes have end portions facing each other near the center of, and with the interposition of, the piezoelectric material, (b) an insulative layer provided on the surface of the first electrode and the surface of the non-electrode portion of the piezoelectric material on the side of the first electrode and, (c) a grounded conductive layer provided on the surface of the insulative layer;
wherein said end portions face each other with a width of about 2 mm or less.

2. The ultrasonic probe according to claim 1, wherein said end portions face each other with the width of 1 mm or less.

3. The ultrasonic probe according to claim 1, wherein a ultrasonic beam width is about 10° or wider.

4. The ultrasonic probe according to claim 1, said conductive layer have a thickness of about 10 μm.

5. The ultrasonic probe according to claim 1, wherein said first electrode has the same potential as the conductive layer.

6. The ultrasonic probe according to claim 1, wherein in a part of the insulative layer, which is in contact with a portion of the ultrasonic wave emitting surface of the piezoelectric element which portion is not covered by the electrode, is made of a material having a large ultrasonic wave attenuation.

7. The ultrasonic probe according to claim 1, wherein the conductive layer is applied in such a way that it covers only a part of the ultrasonic wave emitting surface of the piezoelectric element which part is not covered by the electrode.

8. The ultrasonic probe according to claim 1, wherein the surface of the conductive layer is covered with a protective layer.

9. The ultrasonic probe according to claim 1, wherein a plurality of said piezoelectric elements are aranged in an array fashion.

10. The ultrasonic probe according to claim 9, wherein said piezoelectric elements each have a rectangular shape and the electrodes have the end portions facing each other near the center of a longitudinal direction of each of the rectangular piezoelectric element.

11. The ultrasonic probe according to claim 9, wherein said electrodes have the end portions facing each other near the center of a longitudinal direction of each of the rectangular piezoelectric element, and said portions facing each other are arranged in a straight fashion throughout the arrayed piezoelectric elements.

12. The ultrasonic probe according to claim 1, wherein said first electrode is grounded.

13. The ultrasonic probe according to claim 1, wherein said second electrode is grounded.

* * * * *